(12) United States Patent
Ahn et al.

(10) Patent No.: US 12,016,905 B2
(45) Date of Patent: Jun. 25, 2024

(54) PHARMACEUTICAL COMPOSITION FOR PREVENTION OR TREATMENT OF PRETERM BIRTH

(71) Applicant: KOREA UNIVERSITY RESEARCH AND BUSINESS FOUNDATION, Seoul (KR)

(72) Inventors: Ki Hoon Ahn, Seoul (KR); Eun Jin Wang, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 240 days.

(21) Appl. No.: 17/108,485

(22) Filed: Dec. 1, 2020

(65) Prior Publication Data

US 2021/0162018 A1   Jun. 3, 2021

(30) Foreign Application Priority Data

Dec. 2, 2019   (KR) .......................... 10-2019-0158578

(51) Int. Cl.
| | | |
|---|---|---|
| *A61K 38/39* | (2006.01) | |
| *A61K 31/4439* | (2006.01) | |
| *A61P 15/06* | (2006.01) | |
| *C12Q 1/6881* | (2018.01) | |
| *G01N 33/50* | (2006.01) | |
| *G01N 33/68* | (2006.01) | |

(52) U.S. Cl.
CPC .......... *A61K 38/39* (2013.01); *A61K 31/4439* (2013.01); *A61P 15/06* (2018.01); *C12Q 1/6881* (2013.01); *G01N 33/5023* (2013.01); *G01N 33/5044* (2013.01); *G01N 33/6887* (2013.01); *C12Q 2600/106* (2013.01)

(58) Field of Classification Search
None
See application file for complete search history.

(56) References Cited

PUBLICATIONS

Goldenberg et al. (2008, The Lancet 371:75-84).*
Justice et al., 2016, Disease, Models & Mechanisms 9:101-103.*
Ahn et al., 2017, Am J Perinatol 34(11):1072-1077.*
Lin et al., 2022, NEJM 386(20):933-941.*
Jeong et al., 2021 PLoS One 16(4):e0250108, pp. 1-11.*
Ahn et al., 2021, J Obst Gynaec 41(1):138-146.*
"FN1 Gene," https://www.genecards.org/cgi-bin/carddisp.pl?gene=FN1; accessed Nov. 9, 2023.*
"TGF-beta/Smad" https://www.selleckchem.com/TGF-beta.html?gclid=EAIaIQobChMIha32-4S1ggMVGYrlCh0ytAnUEAAYASAAEgKBj_D_BwE; accessed Nov. 9, 2023.*
"TGFβRI/ALK5 Selective Inhibitors" https://www.selleckchem.com/subunits/TGFbetaRI/ALK5_TGF-beta/Smad_selpan.html; accessed Nov. 9, 2023.*
Lis et al. (2014, Arch Med Sci 10(6):1175-1185).*
Kohno et al. (2007, J investing Dermatol Symp Proc 12(1): 5-8).*
Wang, Eun-jin et al., Effect of TGF-β1 inhibitor (SB 431542) on myofibroblast differentiation of mouse uterine cervical fibroblasts, Korean Society of Maternal Fetal Medicine, 25th Symposium, 2019, p. 6.
Park, Jung Eun et al.; "Effect of fibronectin on protein expression of α-SMA and collagen in mouse uterine cervical fibroblasts"; Department of Obstetrics and Gynecology, Korea University College of Medicine, Seoul, Republic of Korea; 2019.

* cited by examiner

*Primary Examiner* — Elizabeth C. Kemmerer
(74) *Attorney, Agent, or Firm* — Dilworth IP, LLC

(57) ABSTRACT

Disclosed is a pharmaceutical composition for the prevention or treatment of preterm birth, comprising, as an active ingredient, an agent that inhibits the differentiation of fibroblasts into myofibroblasts in cervix.

4 Claims, 11 Drawing Sheets
Specification includes a Sequence Listing.

SEQUENCE LISTING

```
<160> NUMBER OF SEQ ID NOS: 1

<210> SEQ ID NO 1
<211> LENGTH: 2387
<212> TYPE: PRT
<213> ORGANISM: Artificial Sequence
<220> FEATURE:
<223> OTHER INFORMATION: Plasma Fibronectin NP_001157250

<400> SEQUENCE: 1

Met Leu Gly Gly Pro Gly Pro Gly Leu Leu Leu Leu Leu Ala Val Leu
1               5                   10                  15

Ser Leu Gly Thr Ala Val Pro Ser Ala Gly Ala Ser Lys Ser Arg Arg
            20                  25                  30

Gln Ala Gln Gln Ile Val Gln Pro Gln Ser Pro Leu Thr Val Ser Gln
        35                  40                  45

Ser Lys Pro Gly Cys Tyr Asp Asn Gly Lys His Tyr Gln Ile Asn Gln
    50                  55                  60

Gln Trp Glu Arg Thr Tyr Leu Gly Ser Ala Leu Val Cys Thr Cys Tyr
```

```
                65                  70                  75                  80
Gly Gly Ser Arg Gly Phe Asn Cys Glu Ser Lys Pro Glu Pro Glu Glu
                        85                  90                  95

Thr Cys Phe Asp Lys Tyr Thr Gly Asn Thr Tyr Arg Val Gly Asp Thr
            100                 105                 110

Tyr Glu Arg Pro Lys Asp Ser Met Ile Trp Asp Cys Thr Cys Ile Gly
        115                 120                 125

Ala Gly Arg Gly Arg Ile Ser Cys Thr Ile Ala Asn Arg Cys His Glu
    130                 135                 140

Gly Gly Gln Ser Tyr Lys Ile Gly Asp Thr Trp Arg Arg Pro His Glu
145                 150                 155                 160

Thr Gly Gly Tyr Met Leu Glu Cys Val Cys Leu Gly Asn Gly Lys Gly
                    165                 170                 175

Glu Trp Thr Cys Lys Pro Ile Ala Glu Lys Cys Phe Asp Gln Ala Ala
                180                 185                 190

Gly Thr Ser Tyr Val Val Gly Glu Thr Trp Glu Lys Pro Tyr Gln Gly
            195                 200                 205

Trp Met Met Val Asp Cys Thr Cys Leu Gly Glu Gly Ser Gly Arg Ile
        210                 215                 220

Thr Cys Thr Ser Arg Asn Arg Cys Asn Asp Gln Asp Thr Arg Thr Ser
225                 230                 235                 240

Tyr Arg Ile Gly Asp Thr Trp Ser Lys Lys Asp Asn Arg Gly Asn Leu
                    245                 250                 255

Leu Gln Cys Ile Cys Thr Gly Asn Gly Arg Gly Glu Trp Lys Cys Glu
                260                 265                 270

Arg His Thr Ser Leu Gln Thr Thr Ser Ala Gly Ser Gly Ser Phe Thr
            275                 280                 285

Asp Val Arg Thr Ala Ile Tyr Gln Pro Gln Pro His Pro Gln Pro Pro
        290                 295                 300

Pro Tyr Gly His Cys Val Thr Asp Ser Gly Val Val Tyr Ser Val Gly
305                 310                 315                 320

Met Gln Trp Leu Lys Thr Gln Gly Asn Lys Gln Met Leu Cys Thr Cys
                    325                 330                 335

Leu Gly Asn Gly Val Ser Cys Gln Glu Thr Ala Val Thr Gln Thr Tyr
                340                 345                 350

Gly Gly Asn Ser Asn Gly Glu Pro Cys Val Leu Pro Phe Thr Tyr Asn
            355                 360                 365

Gly Lys Thr Phe Tyr Ser Cys Thr Thr Glu Gly Arg Gln Asp Gly His
        370                 375                 380

Leu Trp Cys Ser Thr Thr Ser Asn Tyr Glu Gln Asp Gln Lys Tyr Ser
385                 390                 395                 400

Phe Cys Thr Asp His Thr Val Leu Val Gln Thr Arg Gly Gly Asn Ser
                    405                 410                 415

Asn Gly Ala Leu Cys His Phe Pro Phe Leu Tyr Asn Asn His Asn Tyr
                420                 425                 430

Thr Asp Cys Thr Ser Glu Gly Arg Arg Asp Asn Met Lys Trp Cys Gly
            435                 440                 445

Thr Thr Gln Asn Tyr Asp Ala Asp Gln Lys Phe Gly Phe Cys Pro Met
        450                 455                 460

Ala Ala His Glu Glu Ile Cys Thr Thr Asn Glu Gly Val Met Tyr Arg
465                 470                 475                 480

Ile Gly Asp Gln Trp Asp Lys Gln His Asp Met Gly His Met Met Arg
                    485                 490                 495
```

```
Cys Thr Cys Val Gly Asn Gly Arg Gly Glu Trp Thr Cys Val Ala Tyr
            500                 505                 510

Ser Gln Leu Arg Asp Gln Cys Ile Val Asp Gly Ile Thr Tyr Asn Val
            515                 520                 525

Asn Asp Thr Phe His Lys Arg His Glu Glu Gly His Met Leu Asn Cys
            530                 535                 540

Thr Cys Phe Gly Gln Gly Arg Gly Arg Trp Lys Cys Asp Pro Val Asp
545                 550                 555                 560

Gln Cys Gln Asp Ser Glu Thr Arg Thr Phe Tyr Gln Ile Gly Asp Ser
            565                 570                 575

Trp Glu Lys Tyr Leu Gln Gly Val Arg Tyr Gln Cys Tyr Cys Tyr Gly
            580                 585                 590

Arg Gly Ile Gly Glu Trp Ala Cys Gln Pro Leu Gln Thr Tyr Pro Asp
            595                 600                 605

Thr Ser Gly Pro Val Gln Val Ile Ile Thr Glu Thr Pro Ser Gln Pro
            610                 615                 620

Asn Ser His Pro Ile Gln Trp Ser Ala Pro Glu Ser Ser His Ile Ser
625                 630                 635                 640

Lys Tyr Ile Leu Arg Trp Lys Pro Lys Asn Ser Pro Asn Arg Trp Lys
            645                 650                 655

Glu Ala Thr Ile Pro Gly His Leu Asn Ser Tyr Thr Ile Lys Gly Leu
            660                 665                 670

Arg Pro Gly Val Val Tyr Glu Gly Gln Leu Ile Ser Val Gln His Tyr
            675                 680                 685

Gly Gln Arg Glu Val Thr Arg Phe Asp Phe Thr Thr Thr Ser Thr Ser
            690                 695                 700

Pro Ala Val Thr Ser Asn Thr Val Thr Gly Glu Thr Thr Pro Leu Ser
705                 710                 715                 720

Pro Val Val Ala Thr Ser Glu Ser Val Thr Glu Ile Thr Ala Ser Ser
            725                 730                 735

Phe Val Val Ser Trp Val Ser Ala Ser Asp Thr Val Ser Gly Phe Arg
            740                 745                 750

Val Glu Tyr Glu Leu Ser Glu Glu Gly Asp Glu Pro Gln Tyr Leu Asp
            755                 760                 765

Leu Pro Ser Thr Ala Thr Ser Val Asn Ile Pro Asp Leu Leu Pro Gly
            770                 775                 780

Arg Lys Tyr Thr Val Asn Val Tyr Glu Ile Ser Glu Glu Gly Glu Gln
785                 790                 795                 800

Asn Leu Ile Leu Ser Thr Ser Gln Thr Thr Ala Pro Asp Ala Pro Pro
            805                 810                 815

Asp Pro Thr Val Asp Gln Val Asp Asp Thr Ser Ile Val Val Arg Trp
            820                 825                 830

Ser Arg Pro Arg Ala Pro Ile Thr Gly Tyr Arg Ile Val Tyr Ser Pro
            835                 840                 845

Ser Val Glu Gly Ser Ser Thr Glu Leu Asn Leu Pro Glu Thr Ala Asn
            850                 855                 860

Ser Val Thr Leu Ser Asp Leu Gln Pro Gly Val Gln Tyr Asn Ile Thr
865                 870                 875                 880

Ile Tyr Ala Val Glu Glu Asn Gln Glu Ser Thr Pro Val Phe Ile Gln
            885                 890                 895

Gln Glu Thr Gly Val Pro Arg Ser Asp Lys Val Pro Pro Arg
            900                 905                 910
```

```
Asp Leu Gln Phe Val Glu Val Thr Asp Val Lys Ile Thr Ile Met Trp
            915                 920                 925

Thr Pro Pro Glu Ser Pro Val Thr Gly Tyr Arg Val Asp Val Ile Pro
        930                 935                 940

Val Asn Leu Pro Gly Glu His Gly Gln Arg Leu Pro Val Ser Arg Asn
945                 950                 955                 960

Thr Phe Ala Glu Val Thr Gly Leu Ser Pro Gly Val Thr Tyr His Phe
                965                 970                 975

Lys Val Phe Ala Val Asn Gln Gly Arg Glu Ser Lys Pro Leu Thr Ala
            980                 985                 990

Gln Gln Ala Thr Lys Leu Asp Ala Pro Thr Asn Leu Gln Phe Ile Asn
        995                1000                1005

Glu Thr Asp Thr Thr Val Ile Val Thr Trp Thr Pro Pro Arg Ala Arg
   1010                1015                1020

Ile Val Gly Tyr Arg Leu Thr Val Gly Leu Thr Arg Gly Gly Gln Pro
1025                1030                1035                1040

Lys Gln Tyr Asn Val Gly Pro Ala Ala Ser Gln Tyr Pro Leu Arg Asn
            1045                1050                1055

Leu Gln Pro Gly Ser Glu Tyr Ala Val Ser Leu Val Ala Val Lys Gly
        1060                1065                1070

Asn Gln Gln Ser Pro Arg Val Thr Gly Val Phe Thr Thr Leu Gln Pro
            1075                1080                1085

Leu Gly Ser Ile Pro His Tyr Asn Thr Glu Val Thr Glu Thr Thr Ile
        1090                1095                1100

Val Ile Thr Trp Thr Pro Ala Pro Arg Ile Gly Phe Lys Leu Gly Val
1105                1110                1115                1120

Arg Pro Ser Gln Gly Gly Glu Ala Pro Arg Glu Val Thr Ser Glu Ser
            1125                1130                1135

Gly Ser Ile Val Val Ser Gly Leu Thr Pro Gly Val Glu Tyr Val Tyr
        1140                1145                1150

Thr Ile Ser Val Leu Arg Asp Gly Gln Glu Arg Asp Ala Pro Ile Val
        1155                1160                1165

Lys Lys Val Val Thr Pro Leu Ser Pro Pro Thr Asn Leu His Leu Glu
    1170                1175                1180

Ala Asn Pro Asp Thr Gly Val Leu Thr Val Ser Trp Glu Arg Ser Thr
1185                1190                1195                1200

Thr Pro Asp Ile Thr Gly Tyr Arg Ile Thr Thr Thr Pro Thr Asn Gly
        1205                1210                1215

Gln Gln Gly Tyr Ser Leu Glu Glu Val Val His Ala Asp Gln Ser Ser
        1220                1225                1230

Cys Thr Phe Glu Asn Leu Ser Pro Gly Leu Glu Tyr Asn Val Ser Val
        1235                1240                1245

Tyr Thr Val Lys Asp Asp Lys Glu Ser Val Pro Ile Ser Asp Thr Ile
    1250                1255                1260

Ile Pro Ala Val Pro Pro Pro Thr Asp Leu Arg Phe Thr Asn Val Gly
1265                1270                1275                1280

Pro Asp Thr Met Arg Val Thr Trp Ala Pro Pro Ser Ser Ile Glu Leu
        1285                1290                1295

Thr Asn Leu Leu Val Arg Tyr Ser Pro Val Lys Asn Glu Glu Asp Val
            1300                1305                1310

Ala Glu Leu Ser Ile Ser Pro Ser Asp Asn Ala Val Val Leu Thr Asn
        1315                1320                1325

Leu Leu Pro Gly Thr Glu Tyr Leu Val Ser Val Ser Ser Val Tyr Glu
```

```
                    1330                1335                1340
Gln His Glu Ser Ile Pro Leu Arg Gly Arg Gln Lys Thr Ala Leu Asp
1345                1350                1355                1360

Ser Pro Ser Gly Ile Asp Phe Ser Asp Ile Thr Ala Asn Ser Phe Thr
                    1365                1370                1375

Val His Trp Ile Ala Pro Arg Ala Thr Ile Thr Gly Tyr Arg Ile Arg
                    1380                1385                1390

His His Pro Glu Asn Met Gly Gly Arg Pro Arg Glu Asp Arg Val Pro
                    1395                1400                1405

Pro Ser Arg Asn Ser Ile Thr Leu Thr Asn Leu Asn Pro Gly Thr Glu
                    1410                1415                1420

Tyr Val Val Ser Ile Val Ala Leu Asn Ser Lys Glu Glu Ser Leu Pro
1425                1430                1435                1440

Leu Val Gly Gln Gln Ser Thr Val Ser Asp Val Pro Arg Asp Leu Glu
                    1445                1450                1455

Val Ile Ala Ala Thr Pro Thr Ser Leu Leu Ile Ser Trp Asp Ala Pro
                    1460                1465                1470

Ala Val Thr Val Arg Tyr Tyr Arg Ile Thr Tyr Gly Glu Thr Gly Gly
                    1475                1480                1485

Ser Ser Pro Val Gln Glu Phe Thr Val Pro Gly Ser Lys Ser Thr Ala
                    1490                1495                1500

Thr Ile Ser Gly Leu Lys Pro Gly Val Asp Tyr Thr Ile Thr Val Tyr
1505                1510                1515                1520

Ala Val Thr Gly Arg Gly Asp Ser Pro Ala Ser Ser Lys Pro Val Ser
                    1525                1530                1535

Ile Asn Tyr Arg Thr Glu Ile Asp Lys Pro Ser Gln Met Gln Val Thr
                    1540                1545                1550

Asp Val Gln Asp Asn Ser Ile Ser Val Arg Trp Leu Pro Ser Ser Ser
                    1555                1560                1565

Pro Val Thr Gly Tyr Arg Val Thr Thr Ala Pro Lys Asn Gly Pro Gly
                    1570                1575                1580

Pro Ser Lys Thr Lys Thr Val Gly Pro Asp Gln Thr Glu Met Thr Ile
1585                1590                1595                1600

Glu Gly Leu Gln Pro Thr Val Glu Tyr Val Val Ser Val Tyr Ala Gln
                    1605                1610                1615

Asn Gln Asn Gly Glu Ser Gln Pro Leu Val Gln Thr Ala Val Thr Asn
                    1620                1625                1630

Ile Asp Arg Pro Lys Gly Leu Ala Phe Thr Asp Val Asp Val Asp Ser
                    1635                1640                1645

Ile Lys Ile Ala Trp Glu Ser Pro Gln Gly Gln Val Ser Arg Tyr Arg
1650                1655                1660

Val Thr Tyr Ser Ser Pro Glu Asp Gly Ile His Glu Leu Phe Pro Ala
1665                1670                1675                1680

Pro Asp Gly Glu Glu Glu Thr Ala Glu Leu Gln Gly Leu Arg Pro Gly
                    1685                1690                1695

Ser Glu Tyr Thr Val Ser Val Val Ala Leu His Asp Asp Met Glu Ser
                    1700                1705                1710

Gln Pro Leu Ile Gly Thr Gln Ser Thr Ala Ile Pro Ala Pro Thr Asn
                    1715                1720                1725

Leu Lys Phe Thr Gln Val Thr Pro Thr Ser Leu Thr Ala Gln Trp Thr
                    1730                1735                1740

Ala Pro Asn Val Gln Leu Thr Gly Tyr Arg Val Arg Val Thr Pro Lys
1745                1750                1755                1760
```

```
Glu Lys Thr Gly Pro Met Lys Glu Ile Asn Leu Ala Pro Asp Ser Ser
            1765                1770                1775

Ser Val Val Val Ser Gly Leu Met Val Ala Thr Lys Tyr Glu Val Ser
        1780                1785                1790

Val Tyr Ala Leu Lys Asp Thr Leu Thr Ser Arg Pro Ala Gln Gly Val
    1795                1800                1805

Val Thr Thr Leu Glu Asn Val Ser Pro Pro Arg Arg Ala Arg Val Thr
1810                1815                1820

Asp Ala Thr Glu Thr Thr Ile Thr Ile Ser Trp Arg Thr Lys Thr Glu
1825                1830                1835                1840

Thr Ile Thr Gly Phe Gln Val Asp Ala Ile Pro Ala Asn Gly Gln Thr
            1845                1850                1855

Pro Ile Gln Arg Thr Ile Arg Pro Asp Val Arg Ser Tyr Thr Ile Thr
                1860                1865                1870

Gly Leu Gln Pro Gly Thr Asp Tyr Lys Ile His Leu Tyr Thr Leu Asn
            1875                1880                1885

Asp Asn Ala Arg Ser Ser Pro Val Val Ile Asp Ala Ser Thr Ala Ile
        1890                1895                1900

Asp Ala Pro Ser Asn Leu Arg Phe Leu Ala Thr Thr Pro Asn Ser Leu
1905                1910                1915                1920

Leu Val Ser Trp Gln Pro Pro Arg Ala Arg Ile Thr Gly Tyr Ile Ile
            1925                1930                1935

Lys Tyr Glu Lys Pro Gly Ser Pro Pro Arg Glu Val Val Pro Arg Pro
            1940                1945                1950

Arg Pro Gly Val Thr Glu Ala Thr Ile Thr Gly Leu Glu Pro Gly Thr
            1955                1960                1965

Glu Tyr Thr Ile Gln Val Ile Ala Leu Lys Asn Asn Gln Lys Ser Glu
            1970                1975                1980

Pro Leu Ile Gly Arg Lys Lys Thr Asp Glu Leu Pro Gln Leu Val Thr
1985                1990                1995                2000

Leu Pro His Pro Asn Leu His Gly Pro Glu Ile Leu Asp Val Pro Ser
            2005                2010                2015

Thr Val Gln Lys Thr Pro Phe Ile Thr Asn Pro Gly Tyr Asp Thr Gly
                2020                2025                2030

Asn Gly Ile Gln Leu Pro Gly Thr Ser Gly Gln Gln Pro Ser Leu Gly
            2035                2040                2045

Gln Gln Met Ile Phe Glu Glu His Gly Phe Arg Arg Thr Thr Pro Pro
            2050                2055                2060

Thr Thr Ala Thr Pro Val Arg His Arg Pro Arg Pro Tyr Pro Pro Asn
2065                2070                2075                2080

Val Asn Glu Glu Ile Gln Ile Gly His Val Pro Arg Gly Asp Val Asp
            2085                2090                2095

His His Leu Tyr Pro His Val Val Gly Leu Asn Pro Asn Ala Ser Thr
            2100                2105                2110

Gly Gln Glu Ala Leu Ser Gln Thr Thr Ile Ser Trp Thr Pro Phe Gln
            2115                2120                2125

Glu Ser Ser Glu Tyr Ile Ile Ser Cys His Pro Val Gly Ile Asp Glu
            2130                2135                2140
```

```
Glu Pro Leu Gln Phe Arg Val Pro Gly Thr Ser Ala Ser Ala Thr Leu
2145                2150                2155                2160

Thr Gly Leu Thr Arg Gly Ala Thr Tyr Asn Ile Ile Val Glu Ala Val
            2165                2170                2175

Lys Asp Gln Gln Arg Gln Lys Val Arg Glu Glu Val Val Thr Val Gly
        2180                2185                2190

Asn Ser Val Asp Gln Gly Leu Ser Gln Pro Thr Asp Asp Ser Cys Phe
    2195                2200                2205

Asp Pro Tyr Thr Val Ser His Tyr Ala Ile Gly Glu Glu Trp Glu Arg
2210                2215                2220

Leu Ser Asp Ser Gly Phe Lys Leu Ser Cys Gln Cys Leu Gly Phe Gly
2225                2230                2235                2240

Ser Gly His Phe Arg Cys Asp Ser Ser Lys Trp Cys His Asp Asn Gly
            2245                2250                2255

Val Asn Tyr Lys Ile Gly Glu Lys Trp Asp Arg Gln Gly Glu Asn Gly
            2260                2265                2270

Gln Met Met Ser Cys Thr Cys Leu Gly Asn Gly Lys Gly Glu Phe Lys
        2275                2280                2285

Cys Asp Pro His Glu Ala Thr Cys Tyr Asp Asp Gly Lys Thr Tyr His
        2290                2295                2300

Val Gly Glu Gln Trp Gln Lys Glu Tyr Leu Gly Ala Ile Cys Ser Cys
2305                2310                2315                2320

Thr Cys Phe Gly Gly Gln Arg Gly Trp Arg Cys Asp Asn Cys Arg Arg
            2325                2330                2335

Pro Gly Ala Glu Pro Gly Asn Glu Gly Ser Thr Ala His Ser Tyr Asn
            2340                2345                2350

Gln Tyr Ser Gln Arg Tyr His Gln Arg Thr Asn Thr Asn Val Asn Cys
        2355                2360                2365

Pro Ile Glu Cys Phe Met Pro Leu Asp Val Gln Ala Asp Arg Glu Asp
        2370                2375                2380

Ser Arg Glu
2385
```

PHARMACEUTICAL COMPOSITION FOR PREVENTION OR TREATMENT OF PRETERM BIRTH

REFERENCE TO AN ELECTRONIC SEQUENCE LISTING

The contents of the electronic sequence listing (393-012US_SeqID.txt; Size: 19, 008 bytes; and Date of Creation: Nov. 27, 2020) is herein incorporated by reference in its entirety.

The present disclosure relates to a pharmaceutical composition for the prevention or treatment of preterm birth, and in particular, to a pharmaceutical composition capable of preventing preterm birth by inhibiting an increase in a muscle-collagen ratio in proximal cervix.

BACKGROUND OF THE INVENTION

A ratio of preterm birth in pregnancy is 10%, and a preterm birth e tends to increase every year. In addition, preterm birth is the most important cause of neonatal mortality, which affects a low birthrate and a decrease in population.

A history of preterm birth, a short cervix length, multiple pregnancy, elderly pregnancy, infectious diseases, chronic diseases, etc. are known as risk factors for preterm birth, and measurement of the length of the cervix using ultrasound is used as an early predictive test for preterm birth.

Progesterone, Nifedipine, Prometrium, Makena (hydroxyprogesterone caproate), etc. are used as a preventive or therapeutic agent for preterm birth. Among these, progesterone, which is the most widely used, prevents preterm birth by preventing uterine contraction and preterm labor, and has a prophylactic effect for pregnant woman with a short cervix or a history of preterm labor. However, the progesterone has not been proven to be effective for preterm birth caused by causes other than those described above, and cannot be used for a patient with a history of breast cancer, abnormal liver function, or venous thrombosis. Also, all of the existing therapeutic agents for preterm birth are taken after pregnancy when it is diagnosed that a preterm birth has a high risk, and there are not known therapies and drugs that may be taken before pregnancy to lower the risk of preterm birth in advance.

Thus, there is a need for a therapeutic agent that may act as a pharmacological mechanism different from the conventional therapeutic agent for preterm birth, and may be taken before pregnancy to lower the risk of preterm birth in advance.

PRIOR ART DOCUMENT

[Patent Document]
(Patent Document 1) Korea Patent Application Laid-open No. 10-2017-0125708 (Nov. 15, 2017)

A pharmaceutical composition according to an embodiment may lower the risk of preterm birth.

A pharmaceutical composition according to an embodiment may be administered after cervical surgery to recover the damaged cervix, thereby lowering the risk of increased preterm birth.

SUMMARY OF THE INVENTION

An aspect of the present disclosure provides a pharmaceutical composition for the prevention or treatment of preterm birth, comprising, as an active ingredient, an agent that inhibits the differentiation of fibroblasts into myofibroblasts in cervix.

The present inventors found that the risk of preterm birth may increase if a muscle-collagen ratio increases due to an increase in the differentiation of myofibroblasts in proximal site during a regeneration process after injury such as a wound occurred in the cervix, and confirmed that a drug capable of inhibiting the risk of preterm birth may be used as a therapeutic agent for preterm birth. An increase in the muscle-collagen ratio in the proximal cervix may easily cause the cervical dilatation during pregnancy and cause preterm birth. Thus, the increase in the muscle-collagen ratio in the cervix may be inhibited by preventing the fibroblasts from differentiating into the myofibroblasts in the cervix, thereby reducing the possibility of preterm birth.

In an embodiment, the agent may comprise at least one of a transforming growth factor beta1 (TGF-β1) inhibitor and plasma fibronectin.

The present inventors confirmed the effect obtained by administering various candidates known to be used for a wound treatment, and, as a result, confirmed that the TGF-β1 inhibitor or plasma fibronectin may inhibit an increase in the muscle/collagen ratio in the proximal cervix, which is a causal index of preterm birth.

In an embodiment, the TGF-β1 inhibitor may be a compound represented by the following Formula 1:

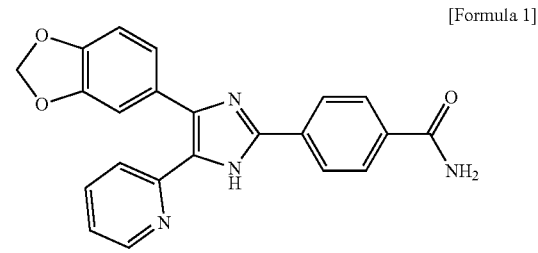 [SMILES: NC(=O)c1ccc(-c2nc(-c3ccc4c(c3)OCO4)c(-c3ccccn3)[nH]2)cc1]

[Formula 1]

The compound represented by Formula 1, also known as SB-431542, has an IUPAC name of 4-(5-benzol[1,3]dioxol-5-yl-4-pyrldin-2-yl-1H-imidazol-2-yl)-benzamide, and a Cas number is 301836-41-9. The SB-431542 is known to inhibit ALK4, ALK5 and ALK7, and an activin/BMP/TGF-β pathway.

The present inventors confirmed that an expression level of α-SMA is decreased by primarily culturing the fibroblasts from the cervix of an animal model of preterm birth, and treating the SB-431542 in step p2.

The plasma fibronectin may be a polypeptide consisting of the amino acid sequence of SEQ ID NO: 1.

Fibronectin is known to play an important role in restoring a tissue as ECM glycoprotein and is classified into plasma fibronectin and cellular fibronectin. Plasma fibronectin and cellular fibronectin have different sequences from each other and may have different effects in preventing preterm birth. Cellular fibronectin is known to promote differentiation into myofibroblasts, but the present inventors confirmed that plasma fibronectin can inhibit the differentiation into myofibroblasts. The origin of the plasma fibronectin is not particularly limited, and for example, a product which is extracted from the bovine plasma and then sterilized may be used, or a commercially available product may be purchased and used.

In an embodiment, the composition may be administrated before pregnancy. The pharmaceutical composition may be administered during pregnancy, but may be administered before pregnancy to prevent preterm birth by inhibiting in advance an increase in the muscle-collagen ratio in the proximal cervix, which is the cause of preterm birth.

In an embodiment, the composition may be for the administration immediately after injury of the cervix. The injury of the cervix includes not only damage caused by surgery such as induced abortion, but also damage that may occur during daily life such as sex, vaginitis, pelvic infection, and damage caused by viral infection. The muscle-collagen ratio in the proximal cervix may be increased even during daily life, and for example, can also be increased by minor damage or inflammation of the cervix that does not require special treatment. Therefore, if the pharmaceutical composition of the present disclosure is administered before pregnancy or immediately after the injury of the cervix, it is possible to effectively prevent preterm birth by blocking an increase in the muscle ratio of the cervix in advance. The term "immediately" may be before recovery after cervical injury, and specifically within 1 hour, 2 hours, 3 hours, 4 hours, 5 hours, 6 hours, 12 hours, 1 It may be within days, within 2 days, within 3 days, within 4 days, within 5 days, within 6 days, or within 7 days.

In one embodiment, the composition may be administered simultaneously or sequentially with an antibiotic or antiviral agent prescribed in case of cervical injury.

The pharmaceutical composition may be formulated and used in the form of, but is not limited to, oral formulation such as powders, granules, capsules, tablets and aqueous suspensions, external preparations, suppositories, patches, and sterile injectable solutions, according to a conventional method. The pharmaceutical composition may comprise a pharmaceutically acceptable carrier. For oral administration, as the pharmaceutical acceptable carrier, binders, lubricants, disintegrants, excipients, solubilizers, dispersants, stabilizers, suspending agents, coloring agents, flavoring agents, etc. may be used. For an injection, as the pharmaceutical acceptable carrier, buffering agents, preservatives, painlessness agents, solubilizers, isotonic agents, stabilizers, etc. may be mixed and used. For topical administration, as the pharmaceutical acceptable carrier, base agents, excipients, lubricants, preservatives, etc.

may be used. The formulation of the pharmaceutical composition may be variously prepared by mixing with a pharmaceutically acceptable carrier as described above. For example, for oral administration, the pharmaceutical composition may be prepared in the form of tablets, troches, capsules, elixirs, suspensions, syrups, wafers, etc., and for an injection, the pharmaceutical composition may be prepared in unit dosage ampoules or multiple dosage forms. Also, the pharmaceutical composition may be formulated as solutions, suspensions, tablets, capsules, sustained-release preparations, etc.

Examples of carriers, excipients and diluents suitable for formulation may include lactose, dextrose, sucrose, sorbitol, mannitol, xylitol, erythritol, malditol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate or mineral oil, etc. In addition, fillers, anti-aggregating agents, lubricants, wetting agents, flavoring agents, emulsifiers, preservatives, etc. may additionally be included.

In an embodiment, the composition may be administered orally, intravenously, intramuscularly, intraarterially, intramedullary, intrathecally, intracardially, transdermally, subcutaneously, intraperitoneally, intranasally, intestinally, topically, sublingually, intracervically, intravaginally, intrauterally, or intrarectally.

In an embodiment, the composition may be administered through a systemic administration route. The systemic administration is a route of administration in which the drug affects the system through the circulatory organs, and may be, for example, oral or injection administration. The systemic administration is distinct from the local administration. According to an embodiment, the composition of the present disclosure exhibited superior effects when administered orally or intraperitoneally, which is systemic administration, than intravaginal administration, which is topical administration.

In an embodiment, the composition may be administered through an administration route, other than intravaginal administration.

According to an embodiment, the composition may be administered orally or by injection, and the injection may be administered intraperitoneally. According to an embodiment, it was confirmed that there is a difference in effect depending on the administration route, and the oral administration or intraperitoneal administration exhibits the effect of lowering the muscle/collagen ratio, which is superior to that of intravaginal administration.

In the present disclosure, "parenteral" includes subcutaneous, intradermal, intravenous, intramuscular, intraarticular, intrasynovial, intrasternal, intrathecal, intralesional, intravaginal, intrauterine, and intracranial injection or infusion techniques. The pharmaceutical composition of the present disclosure may also be administered in the form of suppositories for rectal administration.

Dosage forms for topical or transdermal administration of the compound of the present disclosure may include ointments, pastes, creams, gels, powders, solutions, sprays, inhalants or patches. The active ingredient may be mixed with a pharmaceutically acceptable carrier and any necessary preservatives or buffers under sterile conditions. Ophthalmic formulations, for example, ear drops and eye drops may be included within the scope of the present disclosure. Additionally, the compound of the present disclosure may be used in the form of transdermal patches. Patches can be made by dissolving or dispersing the compound in an appropriate medium. Absorption enhancers may be used to increase the flow of the compound through the skin. The rate of absorption may be controlled by dispersing the compound in a rate controlling film or a polymer matrix or gel.

The pharmaceutical composition may be variously applied, depending on a variety of factors, including the activity of the specific compound used, age, weight, general health, sex, formula, administration time, administration route, excretion rate, drug combination and the severity of specific disease to be prevented or treated. The dosage of the pharmaceutical composition varies depending on the patient's condition and weight, degree of disease, drug form, administration route and administration duration, but may be appropriately selected by those skilled in the art, and may be administered at 0.0001 to 50 mg/kg or 0.001 to 50 mg/kg daily. Administration may be performed once a day, or may be divided several times a day.

The above dosage does not in any way limit the scope of the present disclosure. The pharmaceutical composition according to the present disclosure may be formulated as pill, dragee, capsule, liquid, gel, syrup, slurry, or suspension. The pharmaceutical composition may be prescribed simultaneously or sequentially with a therapeutic agent, an antiviral agent, or an antibiotic, to a patient with cervix-related damage, for example, inflammation such as vaginitis, viral infection, or physical injury, and an increased risk of preterm birth may be prevented by inhibiting the increase in the muscle/collagen ratio in the cervix, which is caused by the injury.

Another aspect of the present disclosure provides a method of preventing or treating preterm birth in a subject thereof, the in need method comprising administering an effective amount of an agent that inhibits the differentiation of fibroblasts to myofibroblasts in cervix.

In an embodiment, the agent may comprises at least one of a transforming growth factor beta1 (TGF-1) inhibitor and plasma fibronectin.

In an embodiment, the TGF-β1 inhibitor may be a compound represented by the following Formula 1:

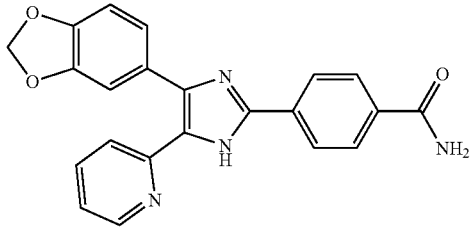

[Formula 1]

In an embodiment, the plasma fibronectin may be a polypeptide consisting of the amino acid sequence of SEQ ID NO: 1.

In an embodiment, the composition may be administered prior to pregnancy.

In an embodiment, the composition is administered immediately after cervical injury.

Another aspect of the present disclosure provides a method of screening an agent for prevention or treatment of preterm birth, the method comprising steps of: contacting fibroblasts isolated from the cervix with a TGF-β1 and a test substance; measuring an expression level of α-SMA in the fibroblasts; and determining the test substance as candidates for the prevention or treatment of preterm birth if the test substance inhibits the expression of α-SMA.

The cervix may be of a mammal, human, or non-human animal, and the specific examples of the non-human animal may include a non-human primate, rodent, pig, mouse, rat, dog, cat, cow, goat, or an animal model of preterm birth.

The fibroblasts may be cells obtained by primarily culturing tissue obtained from the cervix, or by secondarily culturing cells by separating and seeding fibroblasts from primary cultured cells.

The contact of test substance may be performed 12 to 36 hours, 18 to 30 hours, 22 to 26 hours, or 24 hours after the secondary culture.

The α-SMA (alpha smooth muscle actin) is a marker of myofibroblasts, and whether the test substance may inhibit the differentiation of fibroblasts into myofibroblasts may be confirmed by measuring the expression level of α-SMA.

The expression level of α-SMA may be measured at the level of the transcription product by using a method known in the art. For example, mRNA of α-SMA may be quantified by measurement using a probe with a hybridization method or an amplification-based detection method. Alternatively, the expression level of α-SMA may be measured at the level of a protein that is a translation product. The method of measuring the protein may include immunoassay methods known in the art, such as immunoprecipitation using an antibody specifically recognizes the α-SMA protein, Western that blot, immunohistochemical analysis, etc. The antibody may be a monoclonal or polyclonal antibody, and any fragment or modification of the antibody retaining the ability to bind to a target protein may be used.

In an embodiment, the cervix may be a proximal cervix. The cervix may be divided into proximal, middle, and distal cervix, and the muscle/collagen ratio in the proximal cervix is most closely related to the risk of preterm birth. Therefore, the inhibitory effect of the candidate substance on preterm birth may be more accurately confirmed, by measuring the degree of muscle fiber differentiation of fibroblasts obtained from the proximal cervix.

The use of the pharmaceutical composition for preventing or treating preterm birth to according an embodiment may effectively prevent preterm birth by inhibiting an increase in the muscle-collagen ratio in the cervix that causes preterm birth, by administering the composition before or during pregnancy.

DETAILED DESCRIPTION OF THE INVENTION

Hereinafter, one or more embodiments will be described in more detail through examples. However, these examples are only for illustrative purposes and the scope of the present disclosure is not limited to these examples.

Example 1: Production of Animal Model of Preterm Birth

Figure 1:
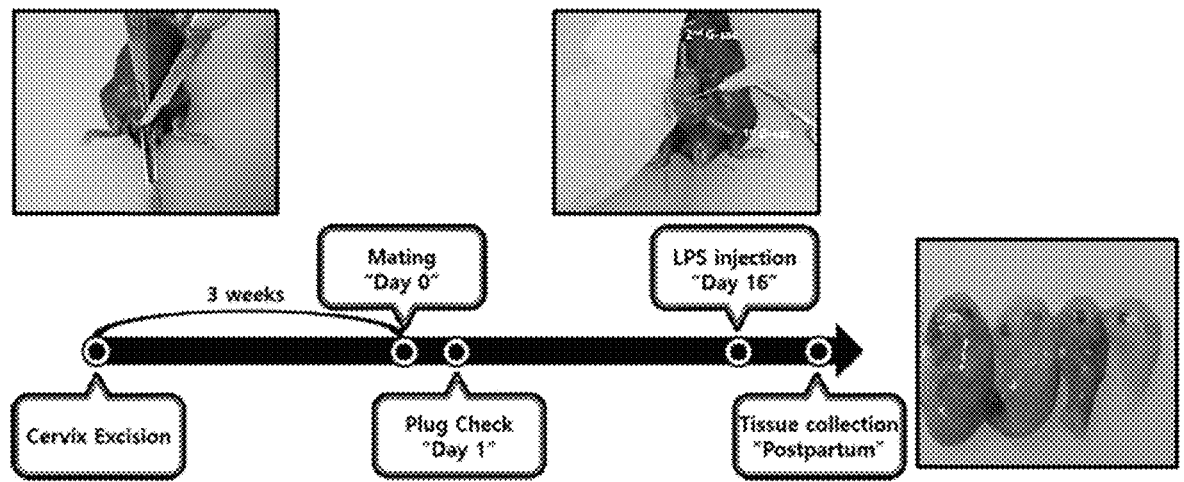
FIG. 1 shows a process of producing an animal model of preterm birth according to an embodiment.

The process of producing an animal model of preterm birth will be described with reference to FIG. 1. Sexually mature female C57BL/6 mice were used in the experiment. The laboratory was maintained at a constant temperature (22 to 24° C.) with a 12-hour day/night cycle.

Mice were randomly assigned to one of four groups, and one group was composed of ten mice. The four groups were divided into A (control, sham), B (cervical partial excision), C (LPS injection), and D (cervical partial excision and LPS injection).

Partial cervical tissue excision was performed at each 5-week old. Specifically, each mouse was anesthetized by inhalation of 2 to 4% isoflurane, and then the cervix thereof was grasped by using forceps, and an excision was made to a depth of 1 mm using a scalpel. In order to minimize bleeding after excision, each mouse was compressed The length of the cervix was 2.5 mm, to stop bleeding. about 40% of the cervix was excised, and an average weight of the excised tissues of cervix was 7 mg. Mating was induced 3 weeks after cervical tissue excision to induce pregnancy, and the probability of pregnancy was about 50%. The day when the mucus plug was in the vagina was set to the first day of pregnancy.

Preterm birth was induced by injecting 100 µg of lipopolysaccharide (LPS, lipopolysaccharide from *Escherichia coli* 055: B5, Sigma-Aldrich)/100 uL of NS between the first and second fetal sacs of right uterus on the 16th day of pregnancy. Twelve hours after delivery, the mice were sacrificed and the uterus was removed.

The mean gestational period was significantly lower in group D, on which both the cervical excision and LPS injection are performed than group A of the control. When delivery was defined as preterm birth within 24 hours after the LPS injection or day 18 before the LPS injection, the proportion of preterm birth was 0% in group A, 30% in group B, 60% in group C, and 100% in group D.

Example 2: Confirmation of Increase in Muscle-Collagen Ratio in Cervix

A sample of cervix was obtained by cutting a portion just above the intersection of the cervix. The tissue of cervix was treated overnight with 4% neutral buffered formalin, fixed, processed, and placed in a paraffin block. Tissue sections (4 µm) were cut from the blocks, mounted on slides, deparaffinized with xylene, and rehydrated with ethanol. Each section was stained with hematoxylin and eosin and the length of the cervix was measured.

To confirm the muscle (smooth muscle)-collagen ratio, histochemical staining was performed using a Masson's trichrome staining kit (NovaUltra). An average percentage of collagen and smooth muscle was analyzed by using Image J software (NIH, Bethesda, MD) for images at 200 magnification for the proximal cervix, middle cervix, and distal cervix regions per section.

Figure 2:
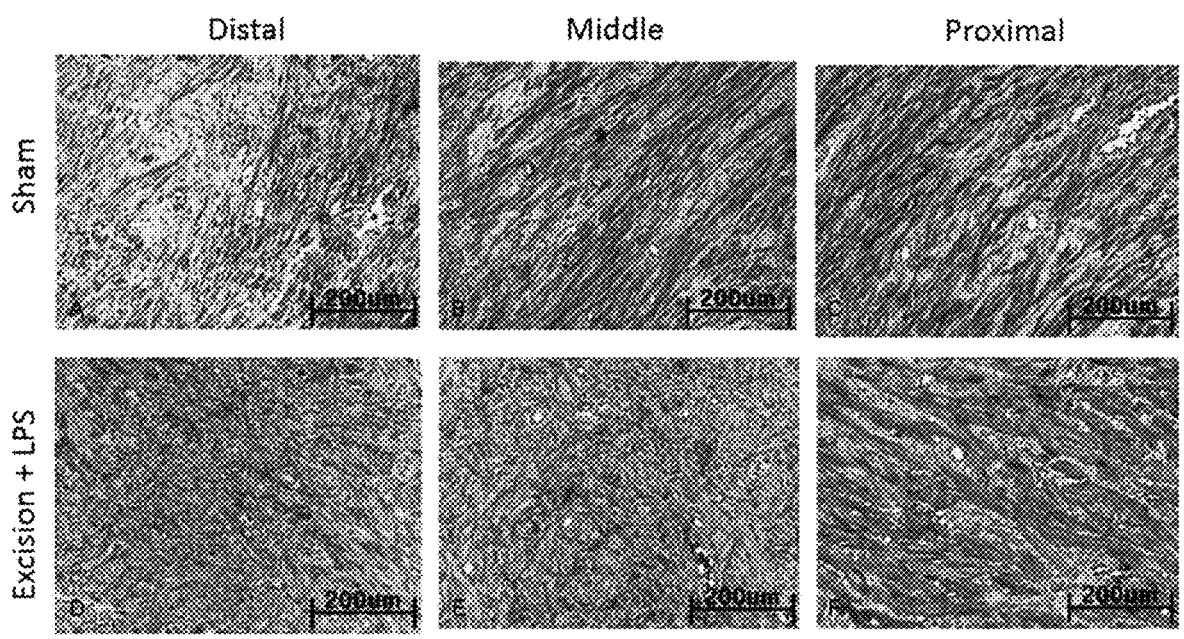
FIG. 2 shows a result of confirming a change in collagen content through Masson's Trichrome histochemical staining for each location in cervix of the animal model of preterm birth according to an embodiment.

FIG. 2 shows a visualization of collagen made by Masson's trichrome staining, which shows that the specific gravity of collagen was reduced in the proximal cervix and the middle cervix of the animal model of preterm birth.

The experimental method to confirm the expression of α-SMA is as follows. The tissue was put in 4% paraformaldehyde for one day and fixed. In order to prevent non-specific binding, the tissue was immersed in a blocking buffer and reacted at room temperature for 5 hours. The primary antibody was mixed and treated with 5% bovine serum albumin (BSA, Sigma, USA) blocking buffer, and then reacted at room temperature. After the completion of a primary antibody reaction, it was washed with 1×PBS, and a secondary antibody (Alexa 488 dye) was mixed and treated with 5% BSA blocking buffer. After the treatment with the secondary antibody, it was washed 3 times with 1×PBS. Since the secondary antibody is sensitive to light, the treatment with the secondary antibody was performed in the dark during the reaction time. All tissue samples were observed through a fluorescence microscope.

Figure 3:
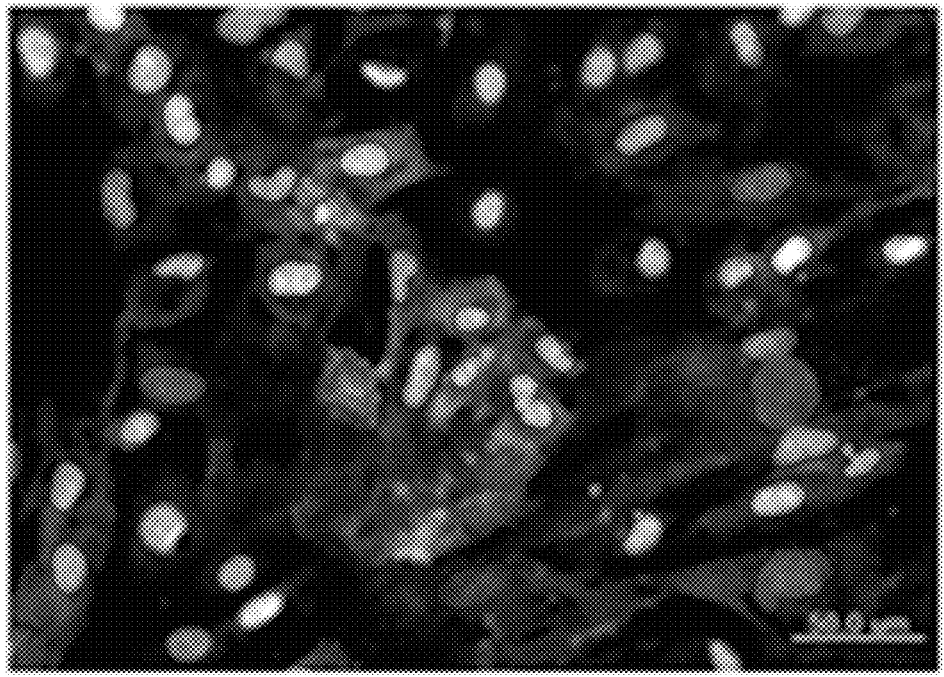
FIG. 3 shows a result of measuring the expression level of the smooth muscle marker,-SMA (alpha-smooth muscle actin) according to an embodiment.
Figure 3:
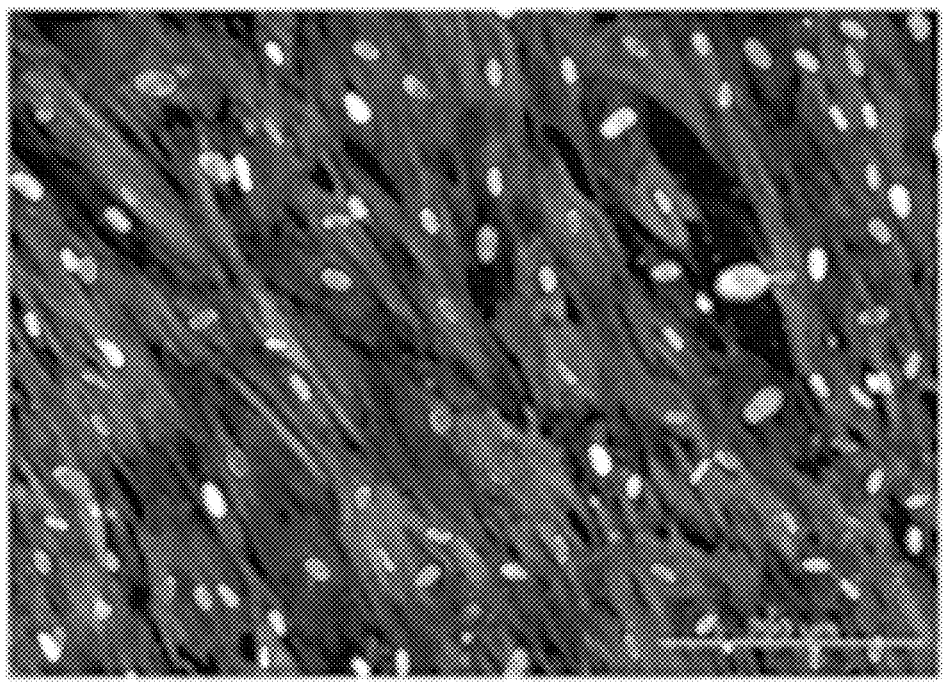

FIG. 3 shows a result of confirming the expression of α-SMA, one of the markers of smooth muscle cells, which shows a significant increase in the expression of α-SMA when cervical excision and LPS infection occurred.

Figure 4:
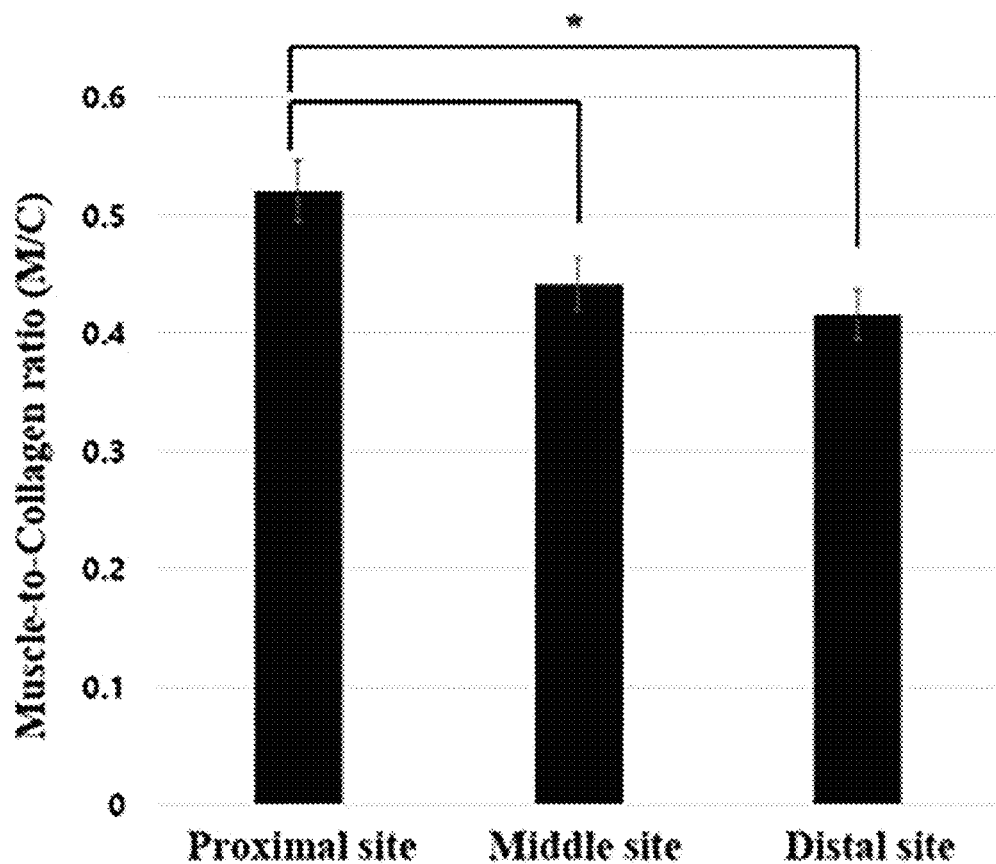
FIG. 4 shows a result of confirming a change in the muscle-collagen ratio in the animal model of preterm birth according to an embodiment.

FIG. 4 shows a result of confirming that the proximal cervix has a higher muscle ratio than the middle cervix and the distal cervix.

According to Table 1 below, it was confirmed that the muscle-collagen ratio in the proximal cervix further increased by up to 65% in group D, on which both an excision of cervical tissue and induction of the inflammatory response by LPS were performed, than those of the other groups.

TABLE 1

|  | A Sham | B Cervical tissue excision | C LPS | D Cervical tissue excision + LPS | p-Value |
|---|---|---|---|---|---|
| Proximal cervix | 0.9 ± 0.5 | 0.8 ± 0.6 | 0.6 ± 0.3 | 1.3 ± 0.6 | 0.037[a] |
| Middle cervix | 0.9 ± 0.7 | 0.7 ± 0.4 | 0.5 ± 0.2 | 1 ± 0.7 | 0.229 |
| Distal cervix | 0.8 ± 0.5 | 0.7 ± 0.4 | 0.4 ± 0.2 | 1.1 ± 0.6 | 0.269 |

It was found that an increase in the ratio of the proximal muscles of the cervix may cause the cervix dilatation during pregnancy, leading to preterm birth.

Example 3: Confirmation of Effects of Reducing Muscle/Collagen Ratio in Cervix Upon Administration of SB431542

Figure 5:
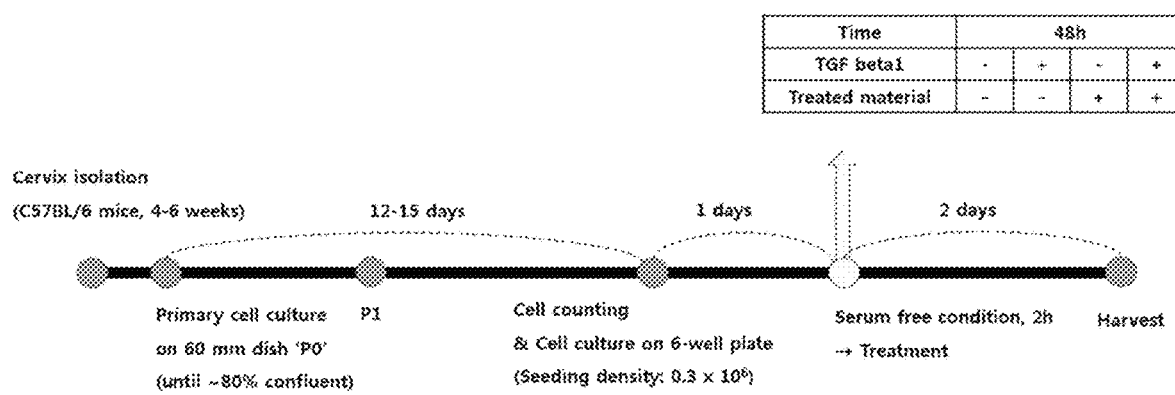
FIG. 5 shows an experimental process of treating fibroblasts isolated from cervical cells of a mouse, with TGF-β1 and SB-431542, which is a TGF-β1 inhibitor, according to an embodiment.

The experiment process will be described with reference to FIG. 5. Cells were isolated from the cervixes of 4- to 6-week old C57BL/6 mice and subjected to primary cell culture in 60 mm dishes (step p0). After step p01 is performed by culturing for 12 to 15 days, the number of fibroblasts was measured, and fibroblasts were seeded in a 6 well dish at a density of about $0.3 \times 10^6$ cells/dish, followed by secondary culture (step p2). After 1 day from the secondary culture, it was treated for 2 hours in a serum-free medium, and then treated with 10 ng/ml of TGF-β1 per dish to induce differentiation into myofibroblasts, and experimental group was treated with SB-431542, which is a TGF-1 inhibitor, at each concentration of 0, 2, 8 and 16 UM. Two days after drug treatment, cells were washed with 10× phosphate buffered saline (PBS; Affymetrix), and proteins were extracted with RIPA buffer. Western blot was performed to investigate the expression levels of α-SMA, a marker of myofibroblasts, and *COLI*, a marker of collagen.

As the primary antibodies, α-smooth muscle actin (1:1000) and type I collagen (1:500) antibody were reacted at 4° C. overnight, and as the secondary antibody, anti-mouse IgG (CellNest, USA) was added thereto and was detected after the reaction for 1 hour at room temperature.

Figure 6:
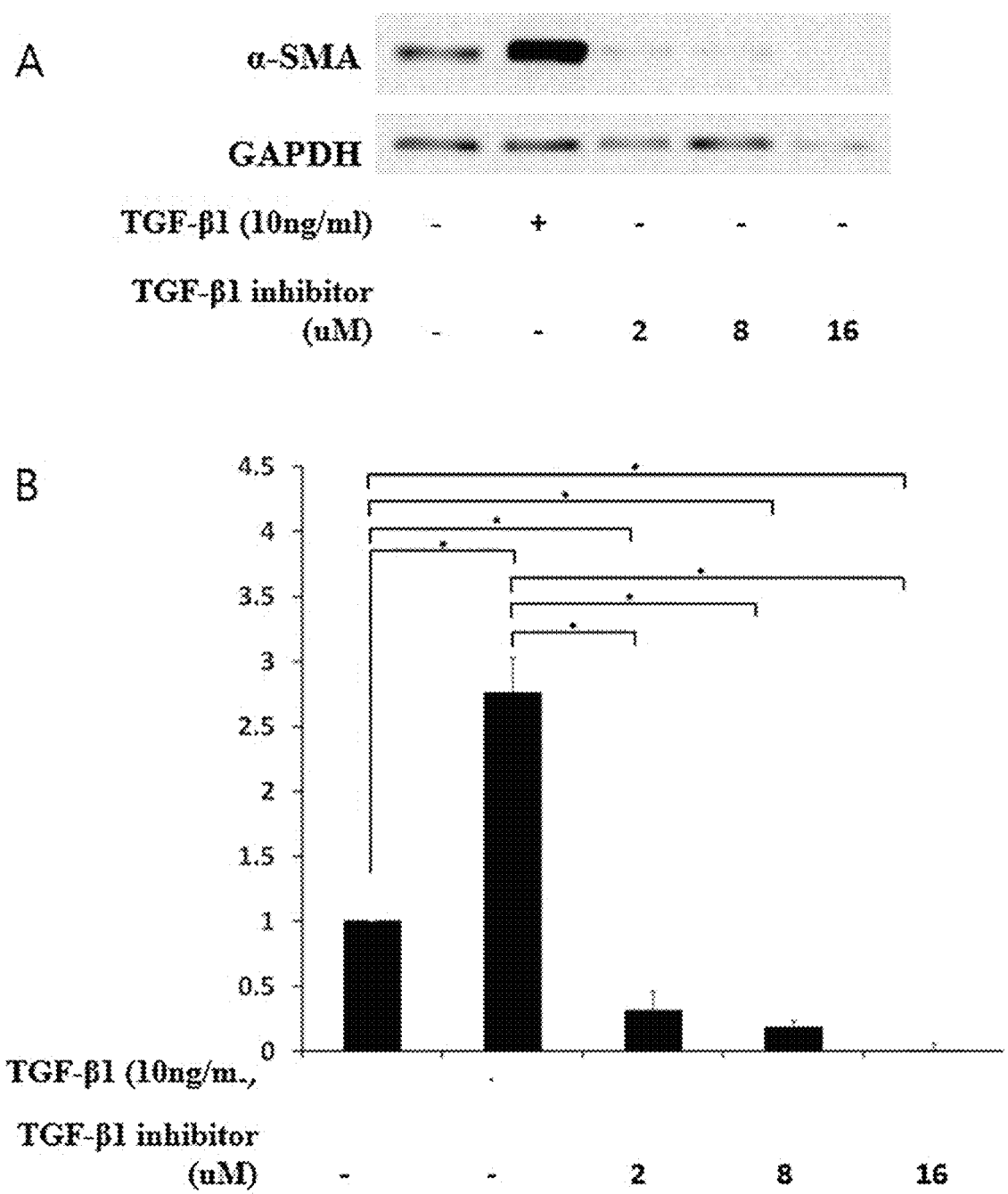
FIG. 6 shows a result of confirming the protein expression level of α-SMA by Western blotting after the experiment of FIG. 5.

Referring to FIGS. 6A and 6B, it could be confirmed that when 8 μM of SB-431542 per dish was treated, the expression of α-SMA protein was reduced, thereby inhibiting differentiation into myofibroblasts. In the subsequent experiment, the experiment was conducted by treating SB-431542 at a concentration of 8 μM/dish based on the dish seeded with $0.3 \times 10^6$ cells.

Figure 7:
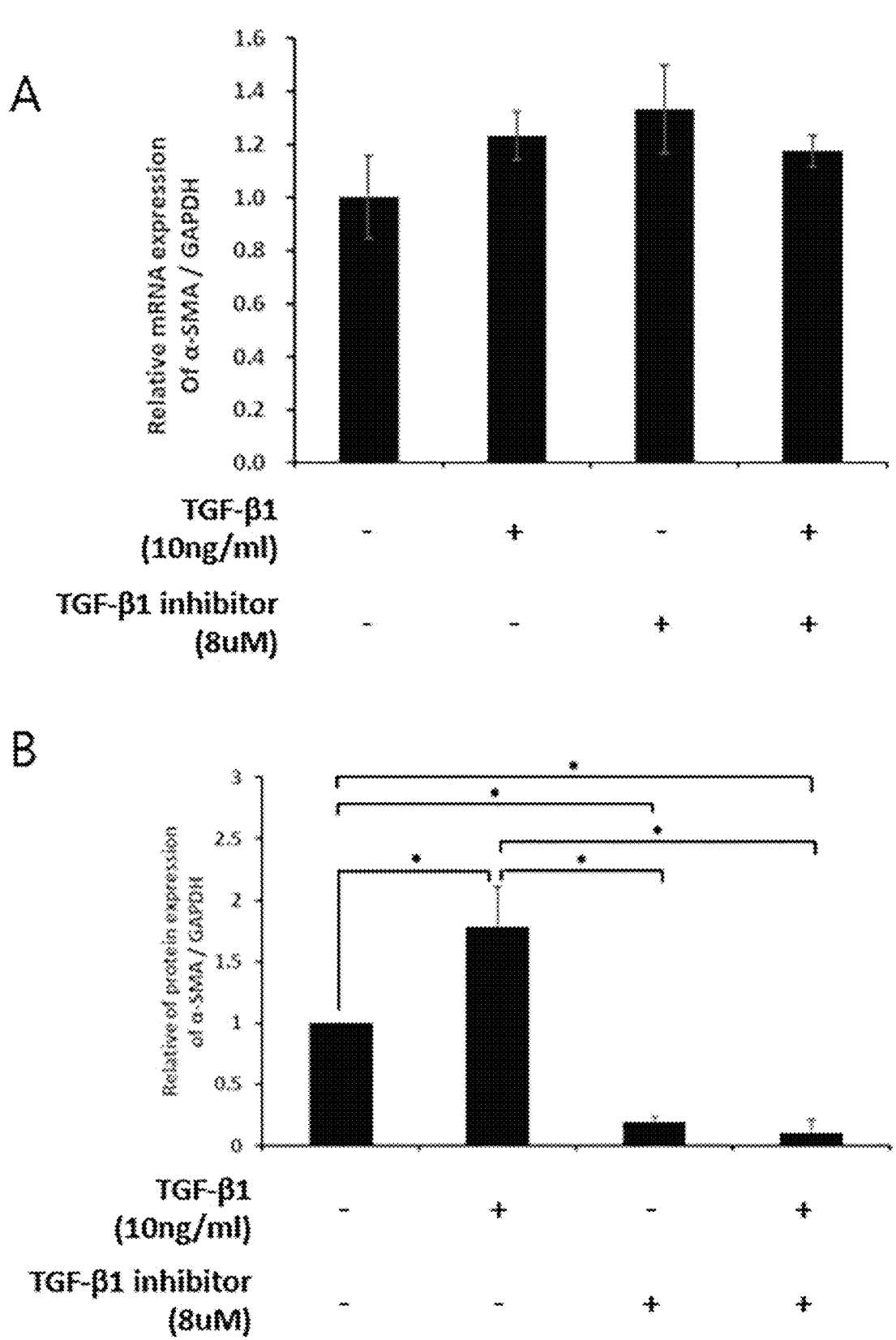
FIG. 7 show a result of confirming the mRNA expression level and the protein expression level of α-SMA after treating fibroblasts, isolated from cervical cells of a mouse, with TGF-β1 and SB-431542, which is a TGF-β1 inhibitor, according to an embodiment.

FIG. 7 shows the results of measuring the mRNA expression level and protein expression level of α-SMA after treating fibroblasts with SB-431542. It was confirmed that according to FIG. 7A, there was no significant change in the mRNA expression level of α-SMA, but according to FIG. 7B, the protein expression level of α-SMA was significantly reduced. Therefore, it could be seen that the treatment with SB-431542 could induce a decrease in the muscle/collagen ratio in the proximal cervix by inhibiting the expression of α-SMA protein.

Figure 8:
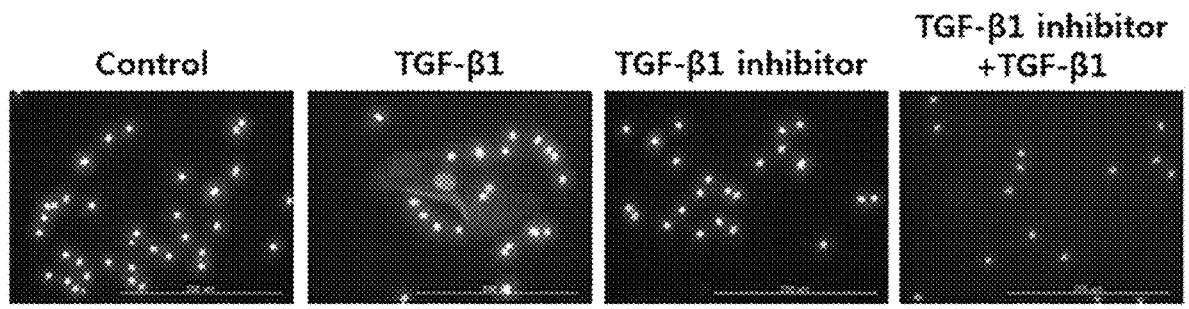
FIG. 8 shows a result of immunofluorescence staining for α-SMA protein after treating fibroblasts isolated from cervical cells of a mouse, with TGF-β1 and SB-431542, which is a TGF-β1 inhibitor, according to an embodiment.

FIG. 8 shows a result of confirming the degree of differentiation into myofibroblasts by measuring the protein expression level of α-SMA by immunofluorescence method. It was confirmed from the result above that if it was treated simultaneously with TGF-β1 and SB-431542, differentiation from fibroblasts to myofibroblasts was inhibited by SB-431542, as the fluorescence detection of α-SMA was reduced.

Figure 9:
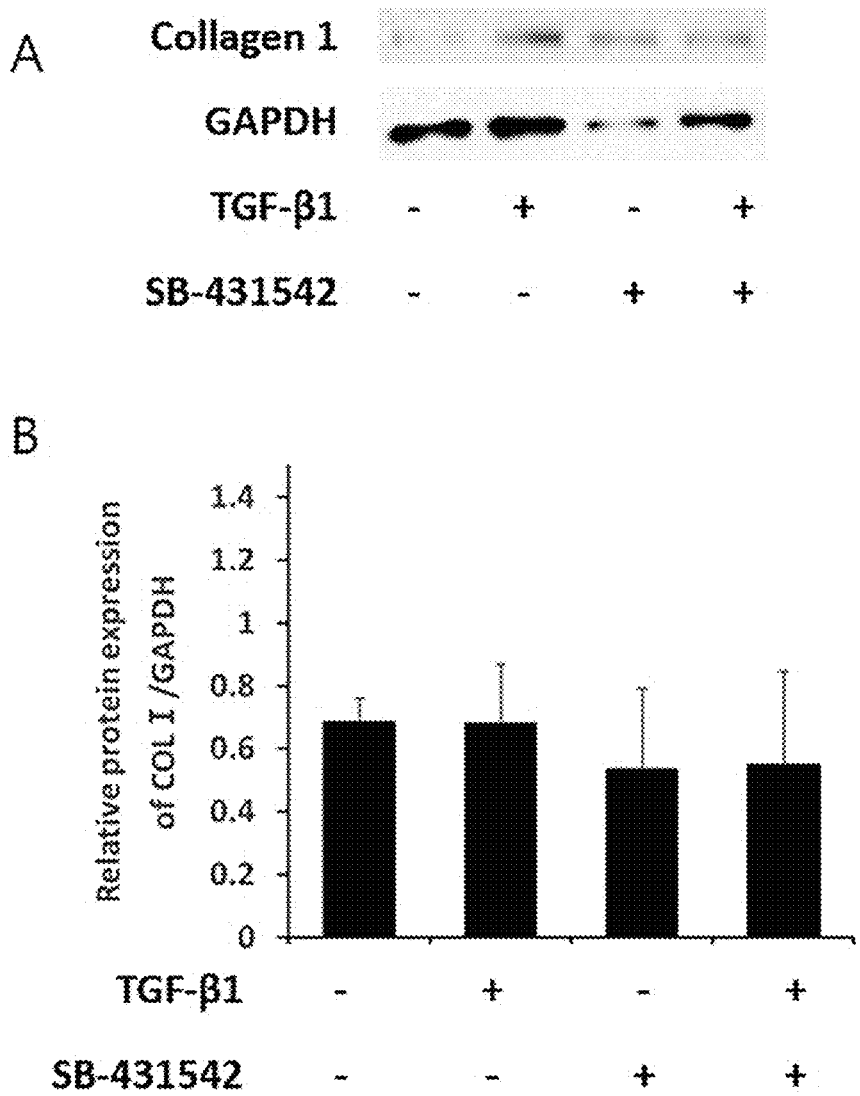
FIG. 9 shows a result of observing a change in expression of collagen 1 after treating fibroblasts isolated from cervical cells of a mouse, with TGF-β1 and SB-431542, which is a TGF-β1 inhibitor, according to an embodiment.

FIG. 9 shows a result of confirming that TGF-β1 and SB-431542, which is a TGF-β1 inhibitor, have no effect on collagen 1 expression.

Taken together with the above experimental results, SB-431542, which is a TGF-β1 inhibitor, inhibits muscle differentiation when administered to the cervix, and does not affect collagen expression. Therefore, SB-431542 may be expected to prevent preterm birth by inhibiting the increase in the muscle-collagen ratio in the proximal cervix, which can occur during cervical injury.

Example 4: Comparison of Effects of Plasma Fibronectin on Decrease in Muscle/Collagen Ratio in Cervix Plasma fibronectin (FN) was administered as a candidate drug capable of inhibiting an increase in the muscle-collagen ratio in the proximal cervix, and changes in the expression levels of α-SMA and type 1 collagen were analyzed. The experiment was performed in the same manner as in Example 3 and FIG. 5, except for the administered drug. For plasma fibronectin, the fibronectin bovine plasma product purchased from Sigma-Aldrich was used, and the dosage thereof was 2 μg/cm2 per well.

Figure 10:
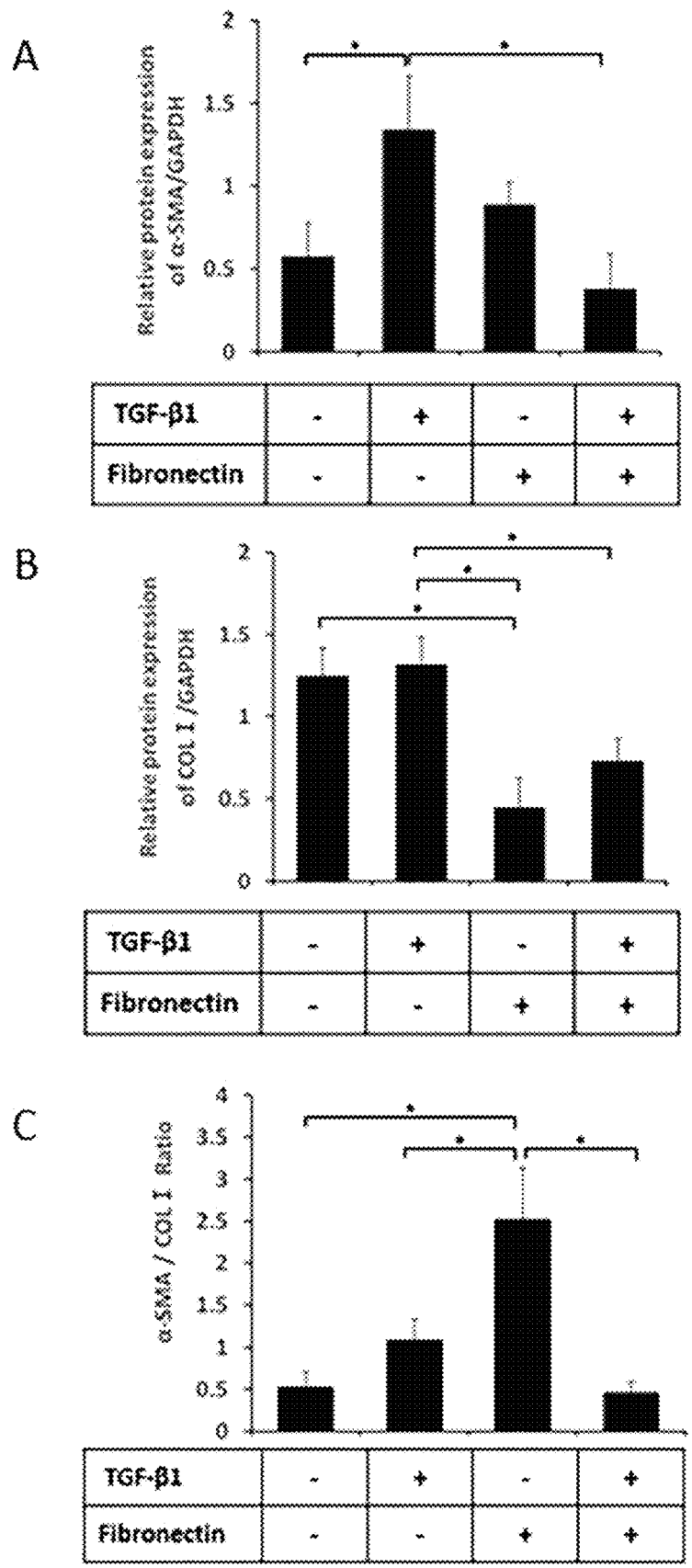
FIG. 10 shows a result of observing a change in the expression level of α-SMA, the expression level of type 1 collagen, and the α-SMA/collagen ratio after treating fibroblasts isolated from cervical cells of a mouse, with TGF-β1 and plasma fibronectin, respectively, according to an embodiment.

It could be confirmed from FIG. 10A that the expression level of α-SMA, which is a differentiation index of muscle cells, was increased by the administration of TGF-β1, but when plasma fibronectin was administered together, the expression level thereof was decreased as much as in the control group wherein TGF-β1 was not administered. In addition, it was confirmed from FIG. 10B that collagen expression was also slightly decreased in the group treated with TGF-β1 and plasma fibronectin together. However, it could be seen from FIG. 10C, which is a result of measuring the ratio of α-SMA and collagen 1 that plasma fibronectin reduced the ratio of α-SMA/collagen 1, which is increased by TGF-β1, and inhibited the increase in the muscle-collagen ratio in the proximal cervix, which may occur during cervical injury, thereby preventing preterm birth.

Example 5: Comparison of Effects of Other Wound Healing Drugs on Decrease in Muscle/Collagen Ratio in Cervix Chondroitin sulfate (CS), tenascin C (TN-C), or TGF-β3, which are drugs used for a wound treatment, were administered, and the inhibitory effect on the increase in the muscle-collagen ratio was confirmed. The experiment was performed in the same manner as in Example 3 and FIG. 5, except for the administered drug.

Chondroitin sulfate was purchased from Sigma-Aldrich, and 50 μg/ml was treated. Tenascin-C was purchased from EMD-Millipore, and 2 μg/ml was treated. TGF-β3 was purchased from Sigma-Aldrich and 10 μg/ml was treated.

Figure 11:
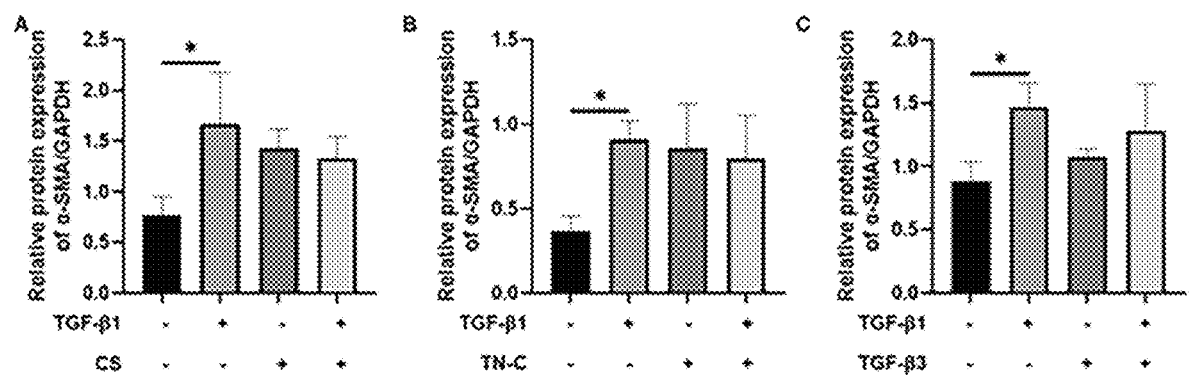
FIG. 11 shows a result of confirming a change in the expression level of α-SMA after treating fibroblasts isolated from cervical cells of a mouse, with a TGF-β1, chondroitin sulfate (CS), tenascin-C(TN-C), and TGF-β3, respectively, according to an embodiment.
Figure 12:
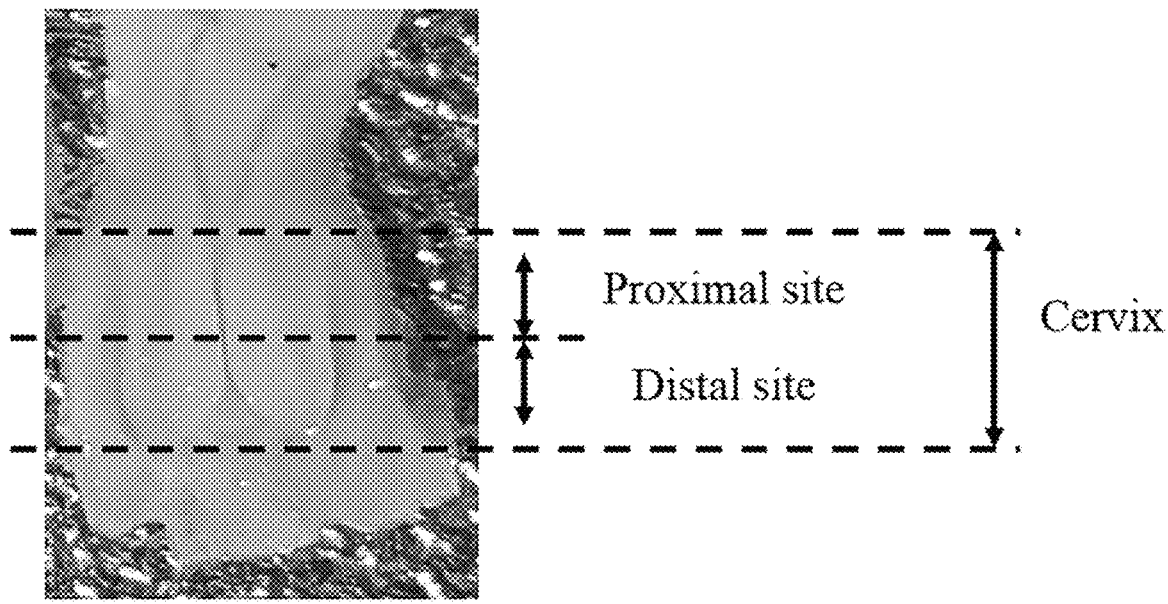
FIG. 12 shows a proximal site and distal site in cervical tissues obtained after intravaginal, oral, and intraperitoneal administration of SB-431542 or fibronectin.

According to FIG. 11, chondroitin sulfate (CS, FIG. 11A), tenascin-C(TN-C, FIG. 11B), and TGF-β3 (FIG. 11C) slightly inhibited the increase in α-SMA expression by TGF-β1, but there was a significant difference from the inhibitory effect of α-SMA expression by SB-431542 (see FIG. 7). Therefore, it was difficult to expect that CS, TN-C, and TGF-β3 would exhibit the effect of inhibiting the expression of α-SMA and the effect of inhibiting the increase in the muscle-collagen ratio in the proximal cervix.

Therefore, it was confirmed that the use of SB-431542 and plasma fibronectin among the existing drugs used for wound healing can have an effect of preventing preterm birth by inhibiting the differentiation of fibroblasts into myofibroblasts in the cervix.

Example 6: Differences in Effects Depending on Drug Administration Route 6-1. A method for intravaginal administration, oral administration (PO), and intraperitoneal administration (IP) of drugs Sexually mature female C57BL/6 mice were used for experiments in vivo. The laboratory was maintained at a constant temperature (22 to 24° C.) with a 12-hour day/night cycle. Partial cervical tissue excision was performed at each 5-week old. Specifically, each mouse was anesthetized by inhalation of 2 to 4% isoflurane, and then the cervix thereof was grasped by using forceps, and an excision was made to a depth of 1 mm using a scalpel. In order to minimize bleeding after excision, each mouse was compressed to stop bleeding. The length of the cervix was 2.5 mm, about 40% of the cervix was excised, and the average weight of the excised tissues was 7 mg.

At the same time as the cervical tissue excision, liquid fibronectin, and SB-431542 dissolved in DMSO were injected into the cervix through the vagina using a feeding needle.

Figure 13:
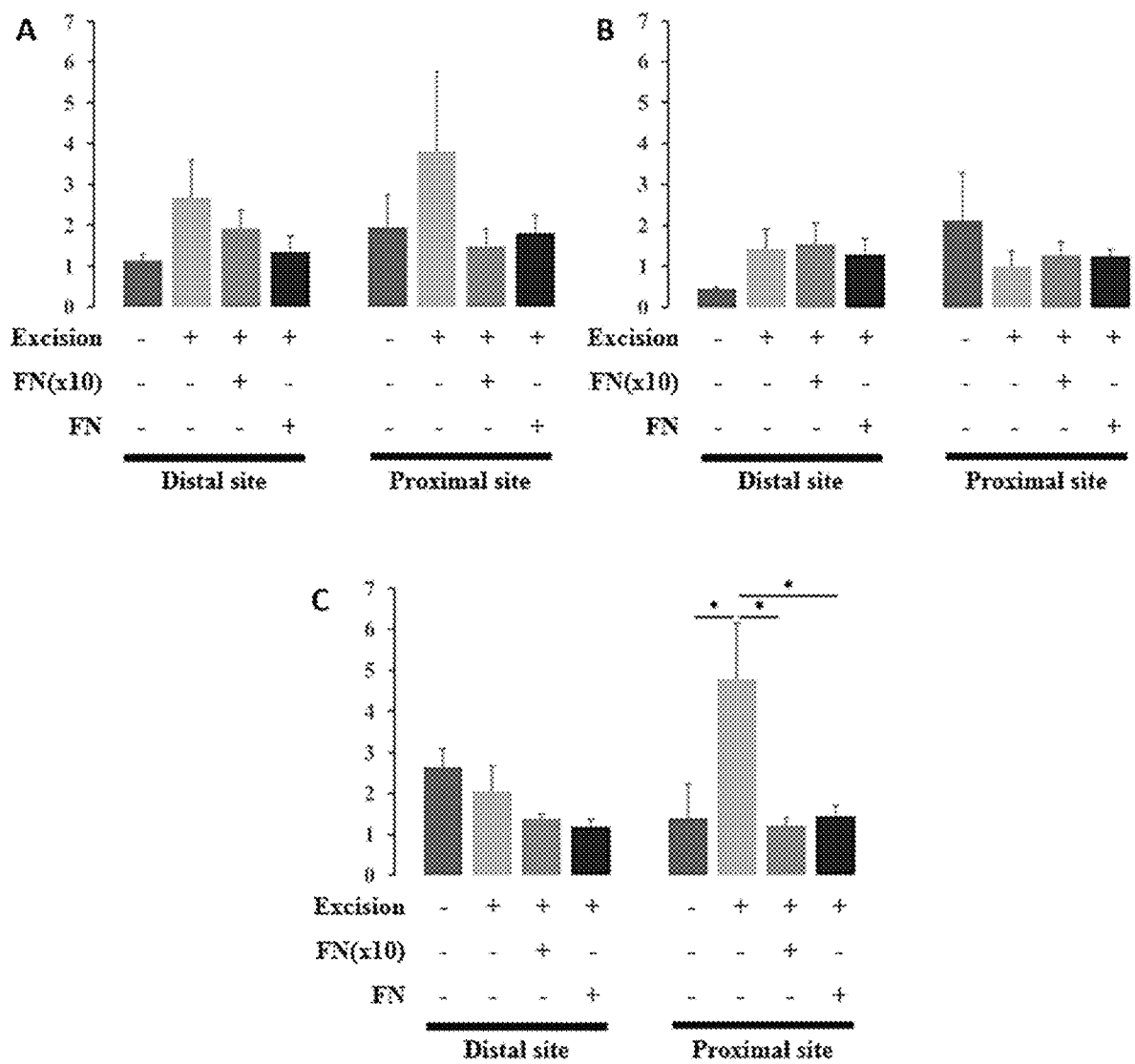
FIG. 13 a result showing α-SMA (A), type I collagen (B), and their ratio (M/C ratio) (C) after the intravaginal administration of fibronectin.

Liquid into the fibronectin (plasma) was infused cervix through the vagina daily for 3 weeks at each dose of 20 mg and 0.2 mg (20 mg, diluted 10 times, expressed as FN (X10)). SB-431542 was dissolved in 5% DMSO, and infused into the cervix through the vagina daily for 3 weeks at each dosage of 20 mg and 0.2 mg (20 mg, diluted 10 times, indicated as SB-431542 (X10). After the drug treatment for 3 weeks, samples were obtained from the proximal cervix and distal cervix regions divided in the cervical tissue (see FIG. 13).

The protein extraction method for confirming the expression of α-SMA and type I collagen (Collagen I) was as follows. After an RIPA buffer (RIPA lysis buffer, 150 mM NaCl, 1% Triton X-100, 1% SD, 0.1% SDS, 50 mM Tris-13 HCl, 2 mM EDTA) and protease inhibitor cocktail (GenDEPOT, P3100-005) were mixed, 100 ul of the mixture was added to separate cervical tissue in each region and pulverized using a homogenizer. After the pulverized product was left on ice for 40 minutes, centrifugation was performed for 15 minutes using a centrifuge (13,000 rpm, 4 degrees). Only the supernatant was used after storage in a new tube. Protein quantification was carried out by a Bradford method (Protein assay dye reagent concentrate buffer, BioRad).

Western blot method for confirming the expression of α-SMA and type I collagen was as follows. The extracted protein was loaded on a 10% SDS PAGE gel at 5 μg each and transferred to a nitrocellulose membrane. After blocking with 5% skim milk, α-smooth muscle actin antibody (1:1000, NSJ Bioreagents, V2001) as the primary antibodies, and type I collagen antibody (1:500, Abcam, ab88147), GAPDH (1:1000, Santa Cruz, sc376559) were reacted at 4° ° C.overnight, and anti-mouse IgG (CellNest, USA) as a secondary antibody was added thereto and reacted for 1 hour at room temperature, and then was developed and detected by using an ECL kit (SuperSignal West Pico PLUS Chemiluminescent Substrate, Thermo Scientific).

For oral administration (PO), the drug was administered to the esophagus through the mouth using a feeding needle at the same time as the cervical tissue excision. SB-431542 was dissolved in 5% DMSO and injected in an amount of 10 mg/kg with each 100 ul for 3 weeks.

For intraperitoneal infusion (IP), the drug was administered intraperitoneally using an insulin syringe at the same time as the cervical tissue excision. SB-431542 was dissolved in 5% DMSO and infused in an amount of 10 mg/kg with each 100 ul for 3 weeks.

For the dosage of SB-431542, reference was made to the paper of Dario in the Nature Medicine "Nilotinib reduces muscle fibrosis in chronic muscle injury by promoting TNF-mediated apoptosis of fibro/adipogenic progenitors."

6-2. Experimental Results

Figure 14:
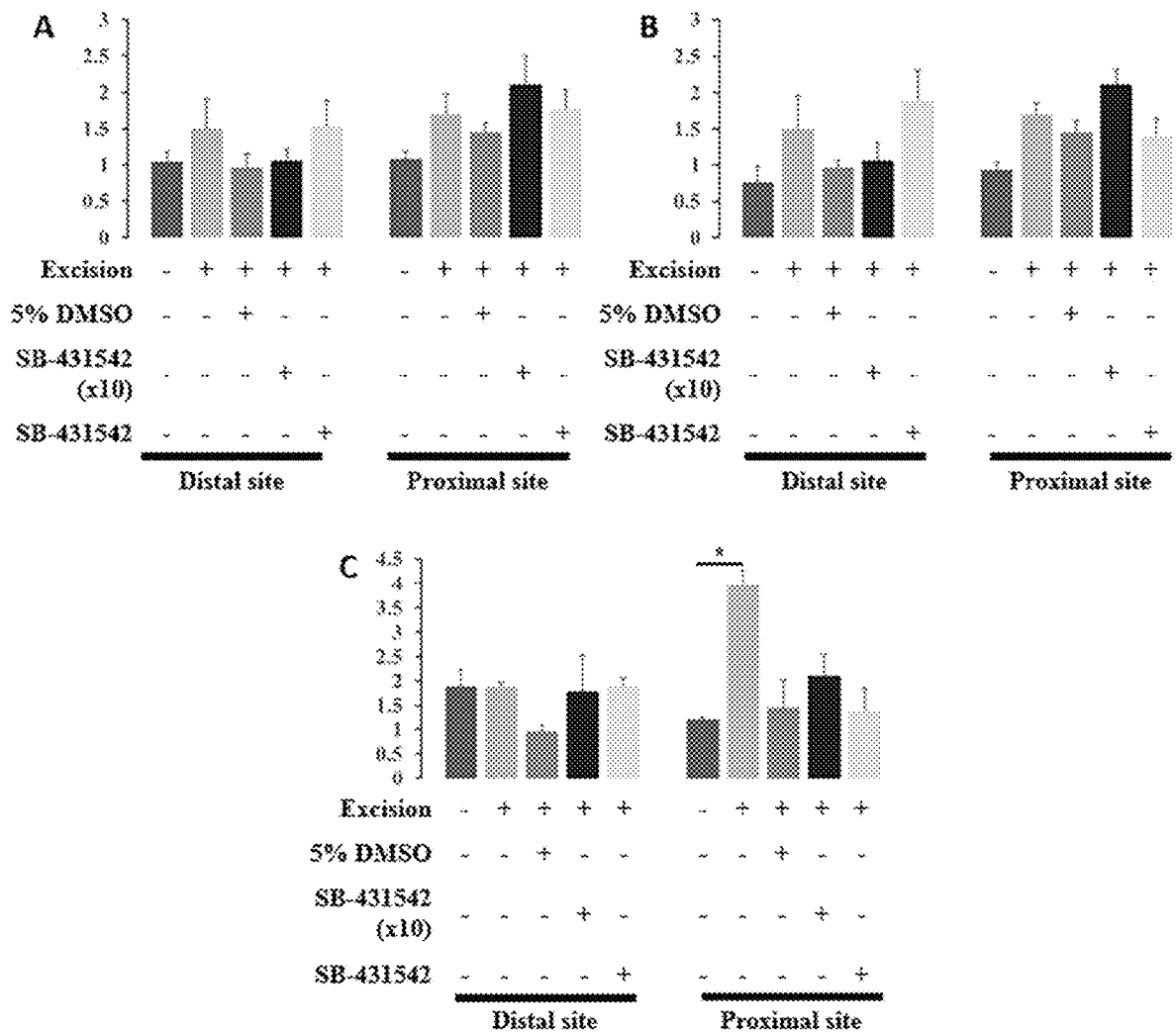
FIG. 14 is a result showing α-SMA (A), type I collagen (B), and their ratio (M/C ratio) (C) after intravaginal administration of SB-431542.

FIG. 14 shows the results after infusing liquid fibronectin into the cervix through the vagina daily for 3 weeks at each dose of 20 mg and 0.2 mg (20 mg, diluted 10 times, expressed as FN (X10)). A is α-SMA, B is type I collagen, and C is an M/C ratio. In FIG. 14C, when it was treated with 20 mg and 0.2 mg of fibronectin, the M/C ratio was decreased compared to the cervical excision group. This is a significant level compared to the control group on which cervical excision was not performed.

Figure 15:
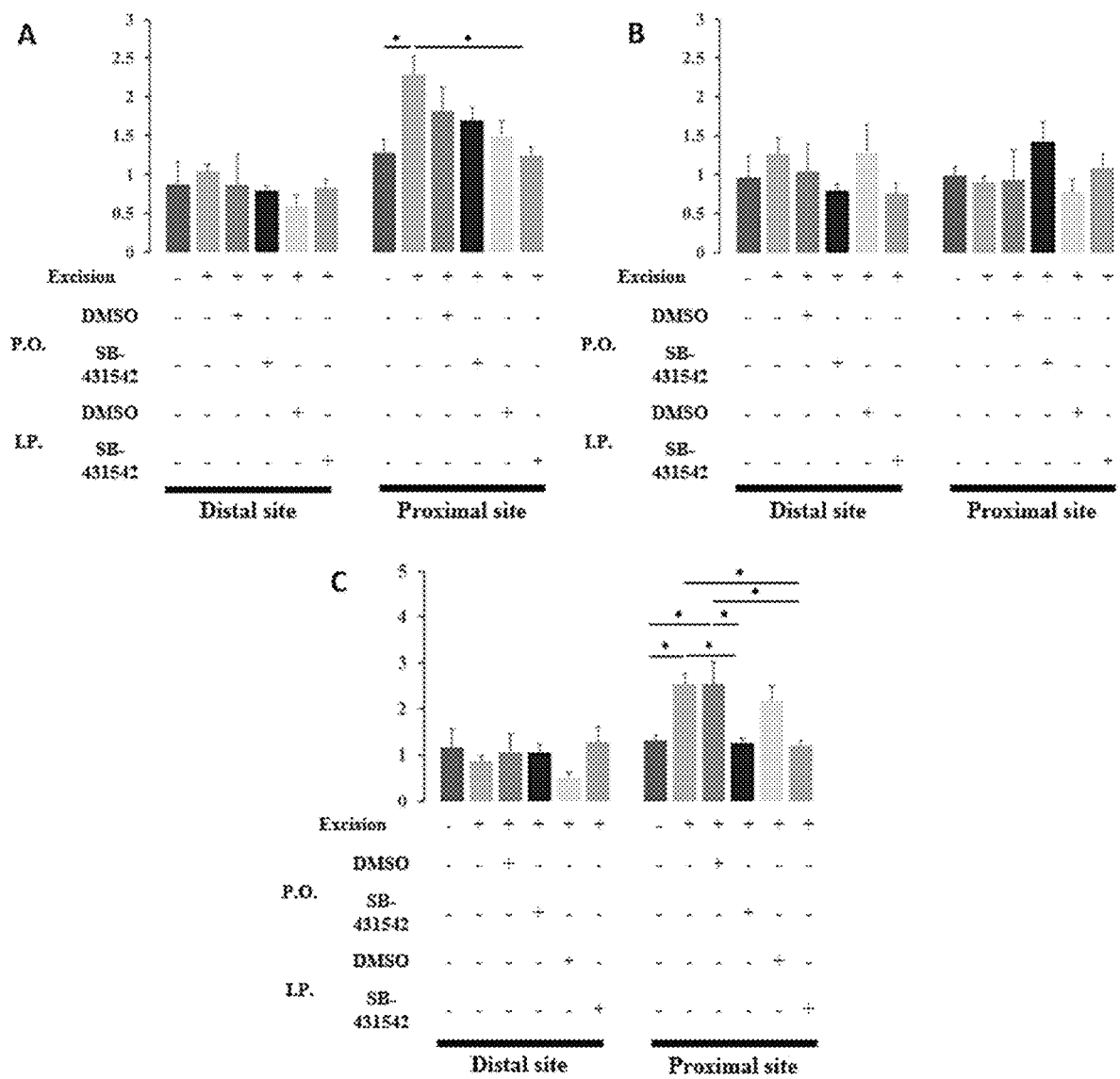
FIG. 15 is a result showing α-SMA (A), type I collagen (B), and their ratio (M/C ratio) (C) after intraperitoneal or oral administration of SB-431542.

FIG. 15 shows the results after infusing SB-431542 into the cervix through the vagina daily for 3 weeks at each dose of 20 mg and 0.2 mg (20 mg diluted 10 times, expressed as SB-431542 (X10)). A is α-SMA, B is type I collagen, and C is an M/C ratio. In FIG. 15C, the cervical excision group had an M/C ratio higher than that of the control group, but there was no significant change in the group treated with 20 mg and 0.2 mg of SB-431542.

FIG. 16 shows the results after drug infusion through oral administration or intraperitoneal infusion of SB-431542 at a dose of 10 mg/kg daily for 3 weeks. A is α-SMA, B is type I collagen, and C is an M/C ratio. In FIG. 16C, the cervical excision group showed an M/C ratio higher than that of the control group, and the group to which DMSO was infused through oral administration showed an M/C ratio similar to that of the control group, whereas the group to which SB-431542 was through administered oral administration or intraperitoneal injection showed an M/C ratio lower than that of the cervical excision group.

The invention claimed is:

1. A method of treating preterm birth in a subject in need thereof, caused by both cervix damage and inflammation of a cervix, the method comprising administering an effective amount of an agent that inhibits the differentiation of fibroblasts to myofibroblasts in the cervix, wherein the agent comprises at least one of a transforming growth factor beta1(TGF-β1) inhibitor and plasma fibronectin
   wherein the TGF-β1 inhibitor is a compound represented by the following Formula 1:

[Formula 1]

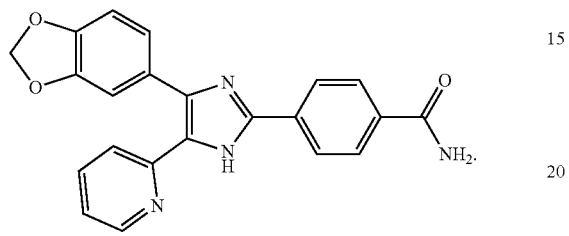

2. The method of claim 1, wherein the plasma fibronectin is a polypeptide consisting of the amino acid sequence of SEQ ID NO: 1.

3. The method of claim 1, wherein the composition is administered prior to pregnancy.

4. The method of claim 1, wherein the composition is administered immediately after cervical injury.

* * * * *